United States Patent
Deininger et al.

(10) Patent No.: US 6,491,713 B1
(45) Date of Patent: Dec. 10, 2002

(54) METHOD AND APPARATUS FOR PLACEMENT OF A BLADDER OUTPUT CONTROL DEVICE

(75) Inventors: Steven T. Deininger, Dellwood, MN (US); James E. Cabak, Plymouth, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 09/286,347

(22) Filed: Apr. 5, 1999

(51) Int. Cl.[7] .............................................. A61B 17/08
(52) U.S. Cl. ........................ 606/213; 604/378; 128/885
(58) Field of Search ............................ 606/213; 604/34, 604/93, 378, 385.17, 514, 11–18, 359; 128/885, DIG. 25, 869; 600/29–31

(56) References Cited

U.S. PATENT DOCUMENTS

| | | | |
|---|---|---|---|
| 3,075,516 A | | 1/1963 | Strauch |
| 4,248,214 A | * | 2/1981 | Hannah et al. ................ 128/7 |
| 5,045,078 A | | 9/1991 | Asta |
| 5,653,700 A | * | 8/1997 | Byrne et al. ................ 604/329 |
| 5,671,755 A | * | 9/1997 | Simon et al. ................ 128/885 |
| 5,954,766 A | | 9/1999 | Zadno-Azizi et al. |
| 6,056,687 A | | 5/2000 | Polyak et al. |
| 6,200,261 B1 | | 3/2001 | Deininger et al. |
| 6,231,501 B1 | | 5/2001 | Ditter |
| 6,258,060 B1 | | 7/2001 | Willard |

FOREIGN PATENT DOCUMENTS

| | | |
|---|---|---|
| EP | 0 862 898 A2 | 9/1998 |
| WO | WO96/00542 A1 | 1/1996 |
| WO | WO99/13801 A1 | 3/1999 |

\* cited by examiner

*Primary Examiner*—Stephen P. Garbe
*Assistant Examiner*—Lien Ngo
(74) *Attorney, Agent, or Firm*—Jeffrey J. Hohenshell

(57) ABSTRACT

A method and apparatus for placing a bladder output control device is disclosed in which a tool has a surface which receives the bladder output control device and holds it for accurate placement of the device on the body of a user. The tool includes an illumination device mounted internal to the tool and provides illumination used in placement of the bladder output control device. The tool further includes a mirrored surface to enable better visualization of where the bladder output control device is located relative to its target location during placement of the device on the body of the user.

30 Claims, 10 Drawing Sheets

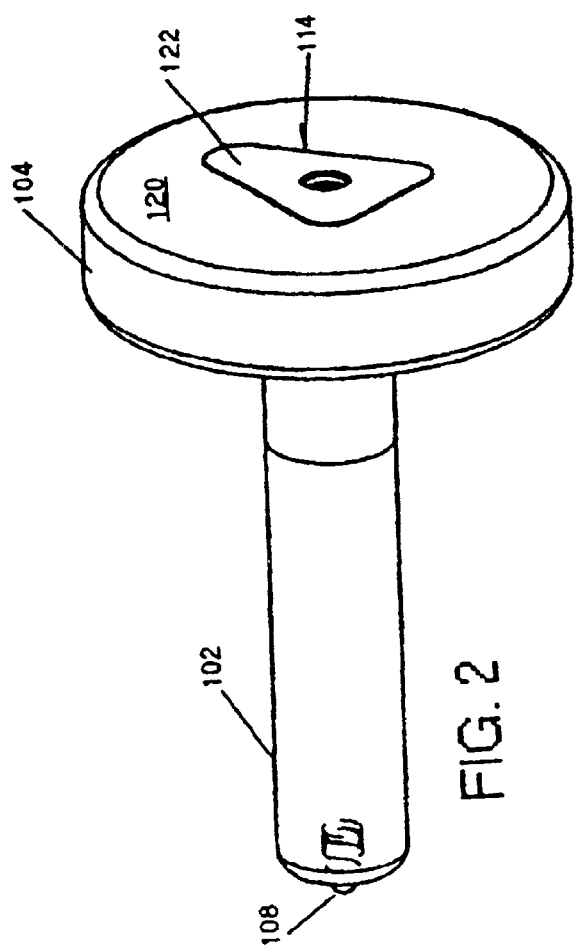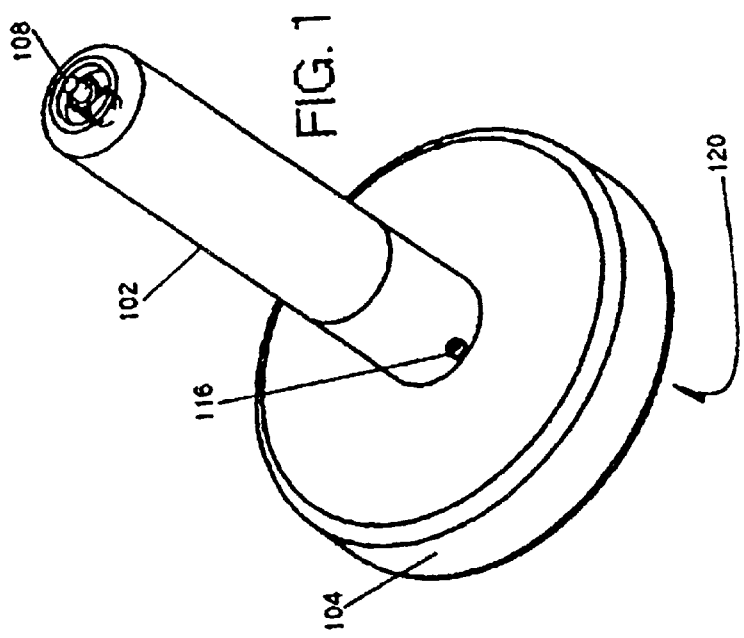

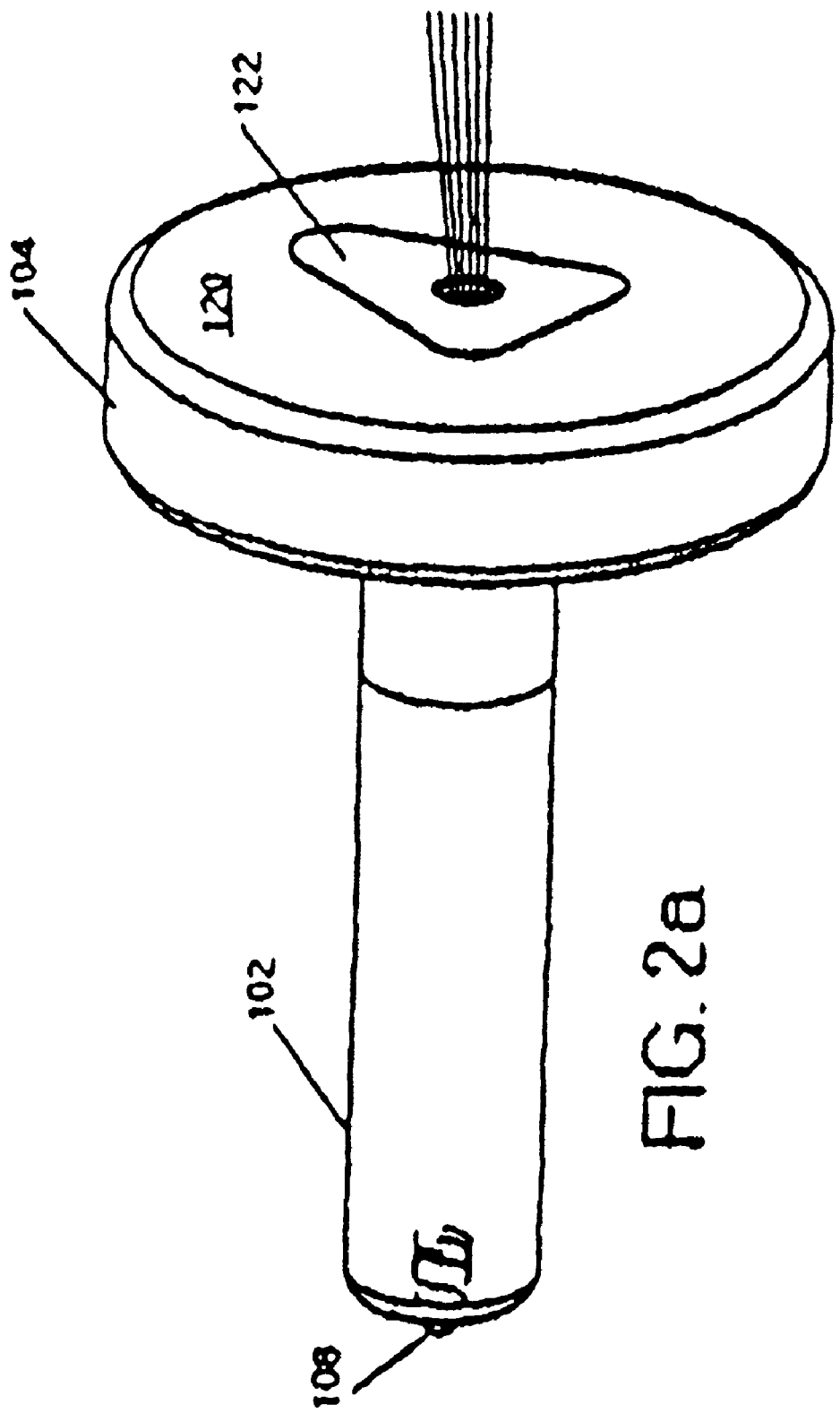

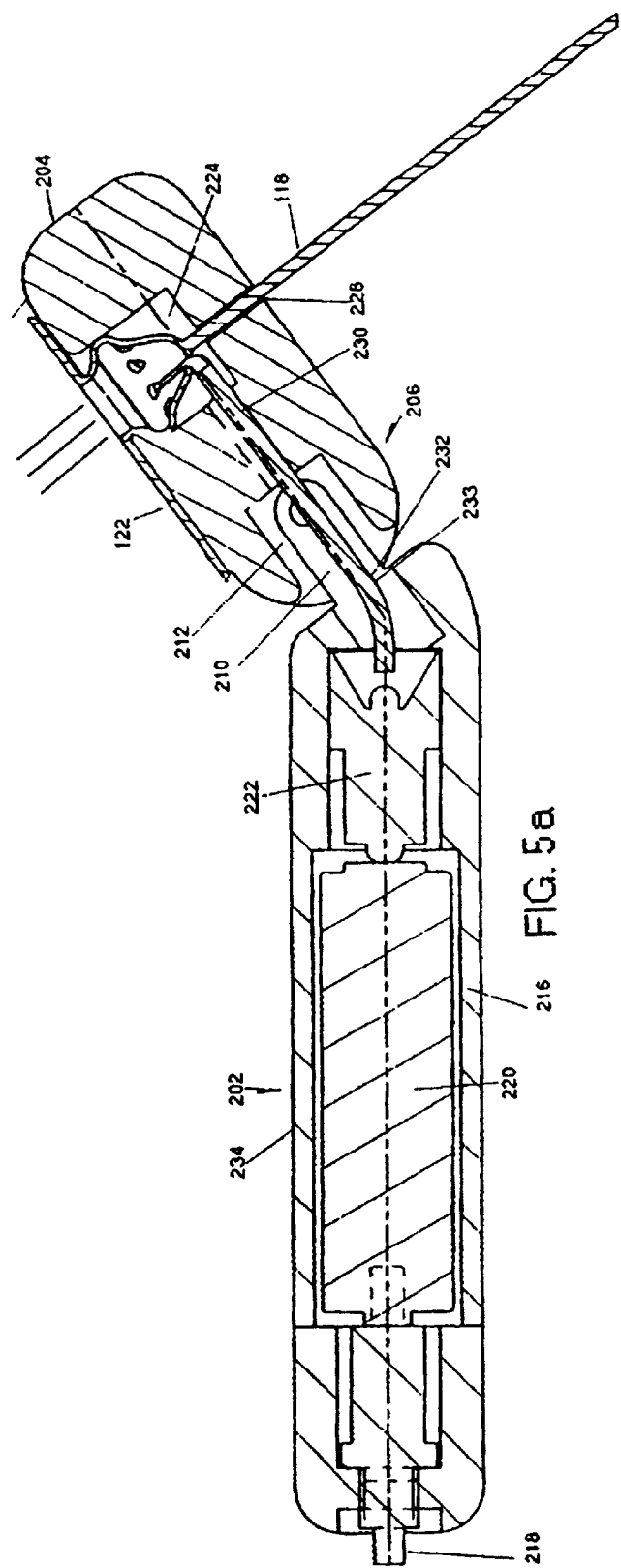

METHOD AND APPARATUS FOR PLACEMENT OF A BLADDER OUTPUT CONTROL DEVICE

FIELD OF THE INVENTION

The present invention relates to an applicator or placement device for use in placing a bladder output control device on the body of a user. The present invention particularly relates to an applicator used for placing a bladder output control device, such as in external incontinence device, on the urinary meatus of a female user. Further, the present invention also relates to a placement device used for placing a bladder output device, such as a urinary catheter, through the urinary meatus and into the bladder.

BACKGROUND OF THE INVENTION

In the course of normal bodily activity, the bladder functions to cyclically store and evacuate urine and thereby effectuate the removal of liquid waste from the body. Although it is not uncommon for the human bladder to operate properly throughout the entire life of an individual, with increasing frequency, individuals are encountering a condition whereby the storage and release of urine is difficult to control with the desired success. Such a condition has been named urinary incontinence and is believed to be one of the most widespread and costly medical conditions prevailing in modem society.

The cause of urinary incontinence is found in the underlying conditions of the bladder or urinary sphincter muscles, which conditions may have varying degrees of complexity. For example, in women, urinary incontinence may be caused by multiple pregnancies, childbirth, and aging that causes a relaxation in the pelvic muscles, which in turn causes incontinence. On the other hand, other causes may include multiple sclerosis, stroke, and spinal cord injuries, all of which disrupt the nerves that control the muscles which control urine retention and evacuation.

Urinary incontinence may be temporary or chronic and there are several options for managing and treating the problem ranging from simply wearing an absorbent pad all the way to submitting to an invasive surgical procedure. Nearly every case of urinary incontinence, however, can be treated with substantial success. As such, it is somewhat surprising that of the approximately 13 million individuals in the United States alone that are suffering from urinary incontinence, less than half seek any medical attention, and fewer than one in ten afflicted individuals are actually treated.

One of the reasons that many instances of urinary incontinence go untreated is that the treatment may be obtrusive, embarrassing or simply inconvenient to the effected patient given the manageability of the condition. Another reason is likely due to costs and the ease with which a particular treatment may be obtained. Accordingly, there have been several previous attempts to arrive at a cost effective, unobtrusive treatment that is readily available to the user, particularly as such treatment relates to female incontinence.

Examples of such treatments may be found in U.S. Pat. No. 5,074,855 and U.S. Pat. No. 5,336,208 which each disclose a device for controlling urinary incontinence in a human female by way of a resilient pad configured to seal against and occlude the urinary meatus of the user. In both patents an adhesive is provided to seal the body of the device against the urinary meatus to hold urine in the bladder. The device is removed and discarded when the user must urinate. Then, after urination, a new device is applied.

Further examples may be found in International Application Nos. 96/39,989, 96/39,990 and 96/39,991, each of which disclose a female urinary incontinence device in the form of a urethral cap with a partially deformable body portion, a hand gripping portion and a body contacting surface. The body portion defines a chamber which allows for a vacuum seal when applied to the patient's body. This device too is removed when the user urinates, at the completion of which the device is then reapplied.

Yet still further examples are found in U.S. Pat. Nos. 6,056,687 and 6,200,261 which are hereby incorporated by reference in their entirety into the present application. These devices are also applied to the body of a female user over the urinary meatus, however, since these devices incorporate an integral valve mechanism, the user need not replace the device with each occurrence of urination but need only open the valve at the time of urination and then close the valve after urination is complete.

Another condition commonly diagnosed in individuals and opposite to urinary incontinence is urinary retention. Urinary retention (whether acute or chronic) may be caused by either an outflow obstruction or poor bladder contractibility. In each case, the oufflow resistance exceeds the pressure generated by contraction of the detrusor muscle that, under normal functioning, pushes the urine out.

Urinary catheterization is a procedure commonly employed to treat and relieve urinary retention. The procedure involves passing a catheter through the urinary meatus and into the bladder. Once the catheter is in the bladder, the balloon is inflated to position and secure the catheter in place. The catheter is then connected to a urine collection bag for closed urinary drainage.

The above-described devices for treatment of urinary incontinence and urinary retention (and other similar products not specifically described) offer many advantages to potential users, including cost effectiveness, availability and convenience. However, it has been discovered that one obstacle or disadvantage to such devices is the potential difficulty encountered in correctly placing and applying such devices to the female body. The location of the urinary meatus is oftentimes very difficult for a user of the device to visualize without assistance, which, in turn, leads to difficulty in placing the incontinence device at the precise location over the urinary meatus, necessary to ensure proper functioning of the device. Specifically for cases involving urinary incontinence, this difficulty is increased if the user is fully clothed and finds herself needing to place the device in the confines of a public restroom facility.

In view of the above, it is apparent that there is a need to provide assistance to the user of bladder output control devices such as those described above that ensures the proper operation of the device and thereby successfully treats the incontinence and retention. Such assistance includes providing better visualization to the user without increasing the effort already required to apply the device. It further includes ensuring that the placement task can be achieved within limited space constraints.

OBJECTS AND SUMMARY OF THE INVENTION

In view of the foregoing, it is an object of the present invention to provide a placement device that addresses the obstacles and disadvantages associated with the consistent and reliable placement of bladder output control device on the body.

A further object of the present invention is to provide a placement device that enables a user to easily visualize the site at which the bladder output device must be placed in order to ensure proper operation of the device.

A further object of the present invention is to provide a placement device that enables the user to place an external incontinence device on the body within the restricted confines of a bathroom facility such as a public toilet stall.

A further object of the present invention is to provide a placement device that is economical to produce and which is readily accessible to potential users.

A further object of the present invention is to provide a placement device that may be used without the assistance of medical care personnel.

A further object of the present invention is to provide a placement device that enables the user to place a catheter through the urinary meatus to the bladder for relief of acute or chronic urine retention.

These and other objects not specifically enumerated herein are believed to be addressed by the present invention which contemplates a device for placement of an external incontinence device which has at least a handle and a surface fixed to the handle which receives the external incontinence device. An illumination device is also included and is mounted on the handle providing illumination at the aforesaid surface.

The present invention further contemplates a tool for placement of an external incontinence device which includes a handle portion for gripping the tool and a flange extending from the handle portion. The flange has a surface for holding the external incontinence device. Further, a compartment is disposed in at least the handle portion for housing an illumination device and the illumination device is positioned in the compartment so as to provide illumination at the surface for holding the external continence device.

The present invention further contemplates a tool for placement of a catheter which includes a handle portion for gripping the tool and a flange extending from the handle portion. The flange has an opening for holding the catheter. Further, a compartment is disposed in at least the handle portion for housing an illumination device and the illumination device is positioned in the compartment so as to provide illumination at the surface adjacent to the distal end of the catheter.

The present invention also contemplates a method of placing an external incontinence device on the body of a user which may includes the steps of holding a handle of a placement tool wherein the handle has a surface for receiving the external incontinence device and then placing the external incontinence device on the surface. The next steps may include directing the external incontinence device toward a urinary meatus of a user and then activating an illumination device mounted on the placement tool either prior to or after the directing step whereby the activation provides illumination at the surface. The following step would likely include visualizing a location of the external incontinence device relative to the urinary meatus and then placing the external incontinence device over the urinary meatus. The final steps would likely include moving the external incontinence device into contact with the body, and then withdrawing the placement tool from the body.

The present invention also contemplates a method of placing a catheter in the body of a user which may includes the steps of holding a handle of a placement tool wherein the handle has a flange with an opening for receiving the catheter and then placing the catheter into the opening. The next steps may include directing the catheter toward a urinary meatus of a user and then activating an illumination device mounted on the placement tool either prior to or after the directing step whereby the activation provides illumination at the surface. The following step would likely include visualizing a location of the catheter relative to the urinary meatus and then directing the catheter through the urinary meatus. The final steps would likely include moving and securing the catheter into the bladder, and then withdrawing the placement tool from the body.

BRIEF DESCRIPTION OF THE DRAWINGS

Other features and advantages of the present invention will be seen as the following description of particular embodiments progresses in conjunction with the drawings, in which:

FIG. 1 is a top perspective view of an embodiment of an applicator/placement device in accordance with the present invention;

FIG. 2 is side perspective view of an embodiment of an applicator/placement device in accordance with the present invention;

FIG. 2a is a side perspective view of another embodiment of an applicator/placement device in accordance with the present invention;

FIG. 5a is a cross-sectional side view of another embodiment of an applicator/placement device in accordance with the present invention;

DETAILED DESCRIPTION OF THE INVENTION

Figure 3:
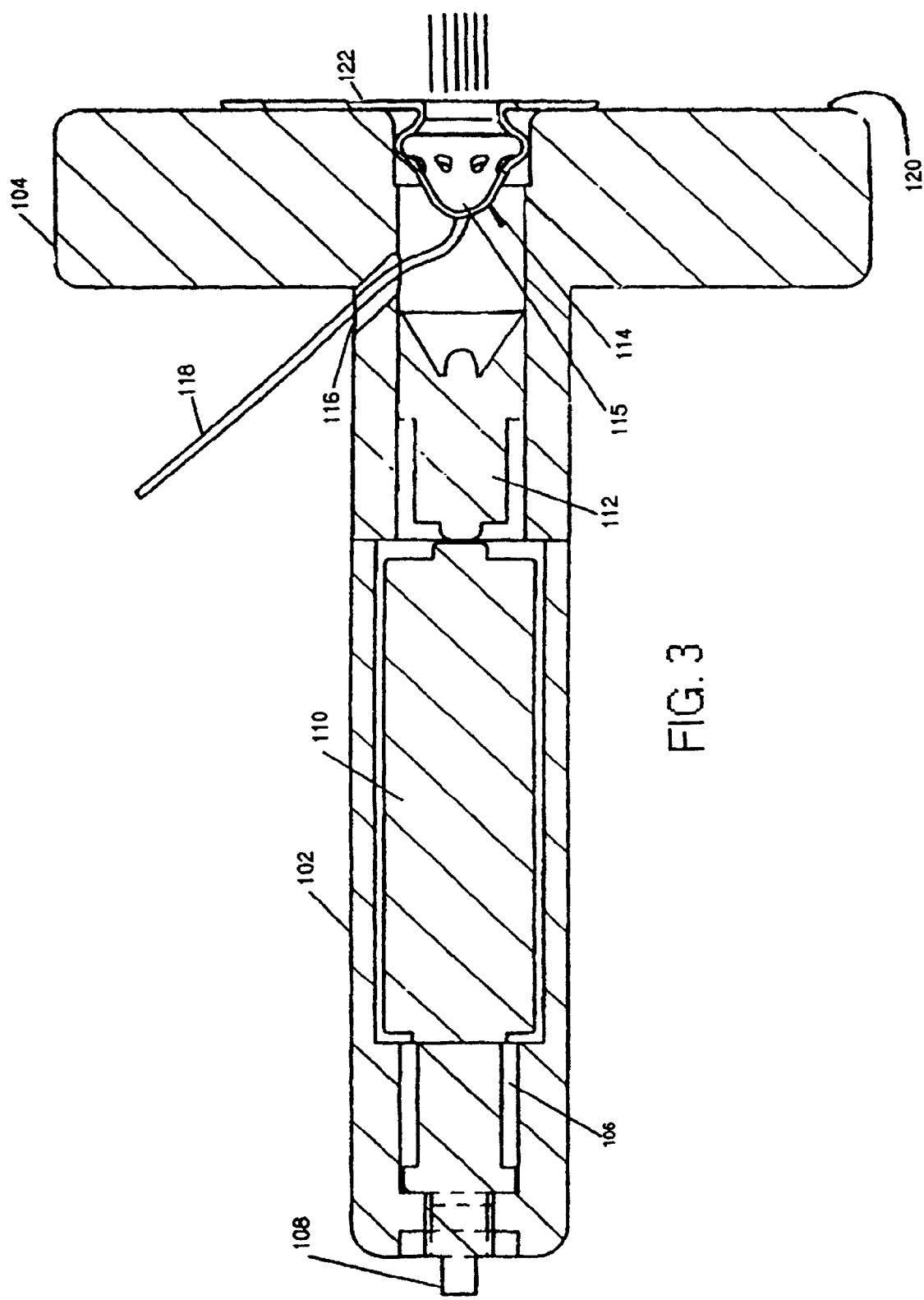
FIG. 3 is a cross-sectional side view of an embodiment of an applicator/placement device in accordance with the present invention the invention.

Referring to FIGS. 1–3, a first embodiment of an applicator or placement device in accordance with the present invention includes a circular handle 102 perpendicularly connected to, and extending from, the center of a circular flange 104. The circular flange 104 is substantially greater in diameter than the circular handle 102 and internal to the circular handle 102 and circular flange 104 is a compartment 106 which extends the length of the handle 102 and the thickness of the flange 104.

The portion of the compartment 106 located in the circular handle 102 contains essentially three components, namely a SPST push-button switch 108 located at the proximal end of the handle 102, a AA size electrical battery 110 located generally in the central portion of the handle 102 and an illumination source 112 located in the distal end of the handle 102. The portion of the compartment 106 located in the circular flange 104 is sized to receive and hold an external continence device 114.

In one embodiment of this disclosed applicator/placement device, the bladder output control device is an external incontinence device 114 which is the same device as that disclosed in U.S. Pat. No. 6,200,261, incorporated herein by reference. As disclosed in that patent, the external incontinence device 114 includes a valve mechanism 115 for selectively opening or closing th e external incontinence device 114 as desired by t he user. However, other types of external incontinence devices can be contemplated for use with this embodiment of the applicator/placement tool.

Referring to FIGS. 1 and 3, at the junction of the circular handle 102 and the circular flange 104 is an access port 116 which extends from the outer surface of the circular handle 102 to the compartment 106. This port 116 is sized to receive the actuation line 118 from the external continence device 114 so that the user may pull the external continence device 114 snugly into the compartment 106. In the operation of the incontinence device 114, the actuation line 118 also serves as the structure for opening the valve 115 of the incontinence device 114.

Referring to FIGS. 2 and 3, the outwardly facing surface 120 of the circular flange 104 serves as the receiving surface for a mounting flange 122 of the external continence device 114. In this disclosed embodiment, the mounting flange 122 is triangular in shape, however, other shapes could also be used.

As mounted on the applicator, the external continence device 114 is positioned such that the valve portion 115 of the device 114 is situated within the compartment 106 of the handle and the underside of the mounting flange 122 is in touching engagement with the outwardly facing surface 120 of the circular flange. This placement is enabled through the tensioning of the actuation line 118 through the access port 116.

In further respect to the circular flange 104, the outwardly facing surface 120 is configured to be a mirrored surface over most if not all of its surface area. In a preferred embodiment, this surface is achieved by sizing a mirror piece to fit on the outwardly facing surface area 120 and then adhering the mirror piece to the outwardly facing surface area 120 by any suitable adhesive means.

In operation, a user will mount the incontinence device 114 onto the applicator/placement tool by inserting the actuation line 118 through the access port 116. The user will then insert the top portion of the incontinence device (in this case the valve portion 115) into the compartment 106 until the underside of the mounting flange 122 is in touching engagement with the outwardly facing surface 120 of the circular flange 104. The user may then apply tension to the actuation line 118 to ensure that the incontinence device is securely mounted onto the tool.

Figure 3A:
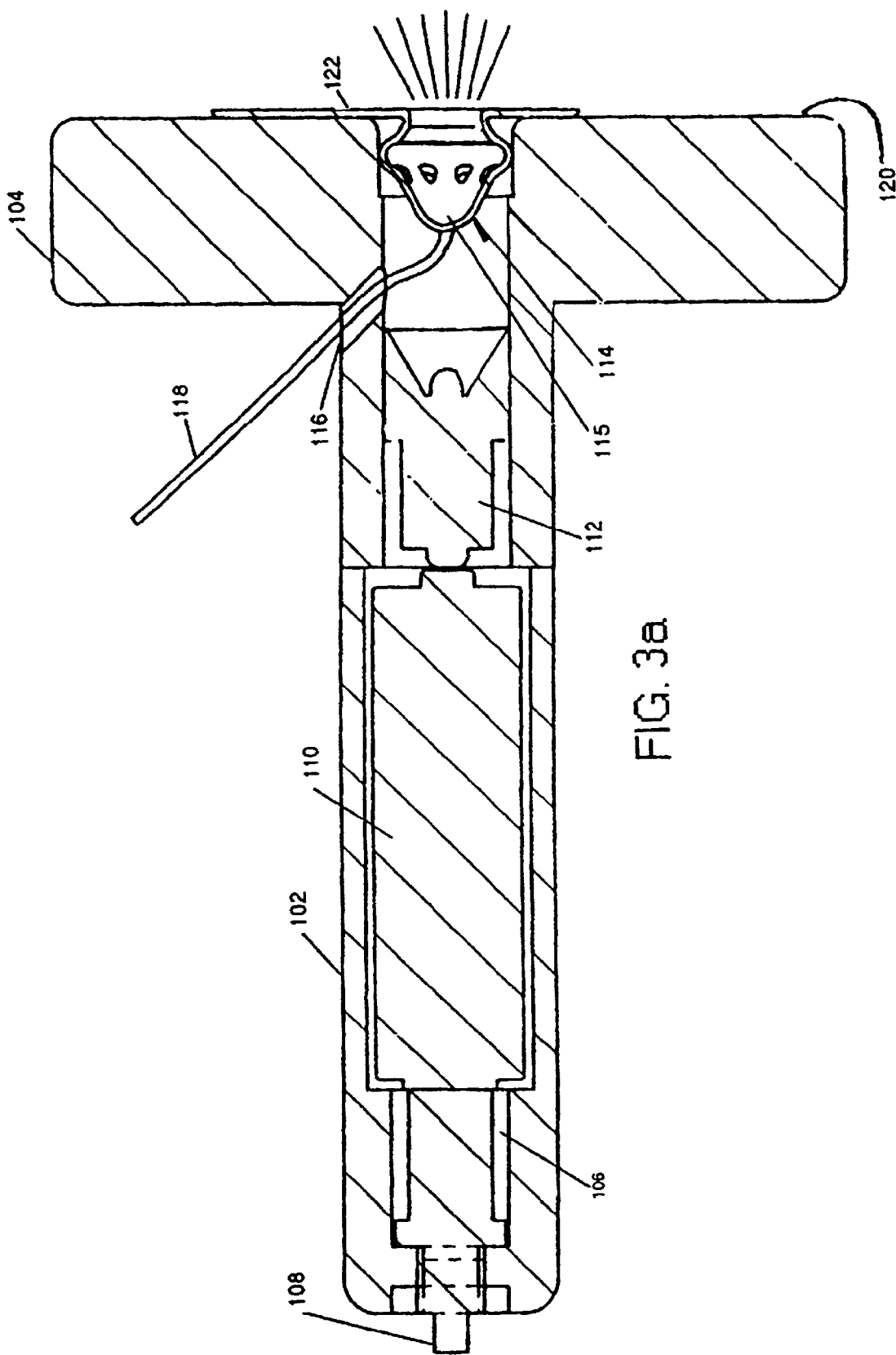
FIG. 3a is a cross-sectional side view of another embodiment of an applicator/placement device in accordance with the present invention the invention.

Once the incontinence device 114 is mounted the user may then actuate the push-button switch 108, which closes the contacts between the battery 10 and the illumination source 112 and causes the illumination source 112 to generate light. Light from the illumination source 112 then travels down through the compartment 106 of the circular flange 104. Since the incontinence device 114 is translucent, a quantity of light from the illumination source 112 will be diffused through the incontinence device 114 so as to provide illumination at the outwardly facing surface 120 of the circular flange 104, as shown in FIG. 3. Alternatively, as shown in FIGS. 2a and 3a, the illumination source 112, possibly in combination with a lens or lenses (not shown), may be configured to generate a focused beam of light through the incontinence device 114. The focused beam of light provides improved illumination at the specific targeted area.

If not previously performed, the user will then remove any protective material from the exposed side of the external incontinence device 114 and expose the adhesive that is coated on the exposed side. The user will then orient the device in a manner such that the light emanating from the compartment 106 of the circular flange 104 is directed toward the urinary meatus.

Furthermore, by positioning the tool at an angle relative to the meatus, the user will be thereby enabled to visualize the meatus and surrounding area on the mirrored, outwardly facing surface 120 of the circular flange 104. Moreover, the user can then position the external continence device 114 in a manner such that the opening for directing the urine can be placed precisely over the meatus. The user will then move the tool so that the adhesive contacts the body. Upon withdrawing the tool, the incontinence device 114 is then removed from the tool and remains secured to the user in a manner that ensures proper treatment of the incontinence.

Figure 3B:
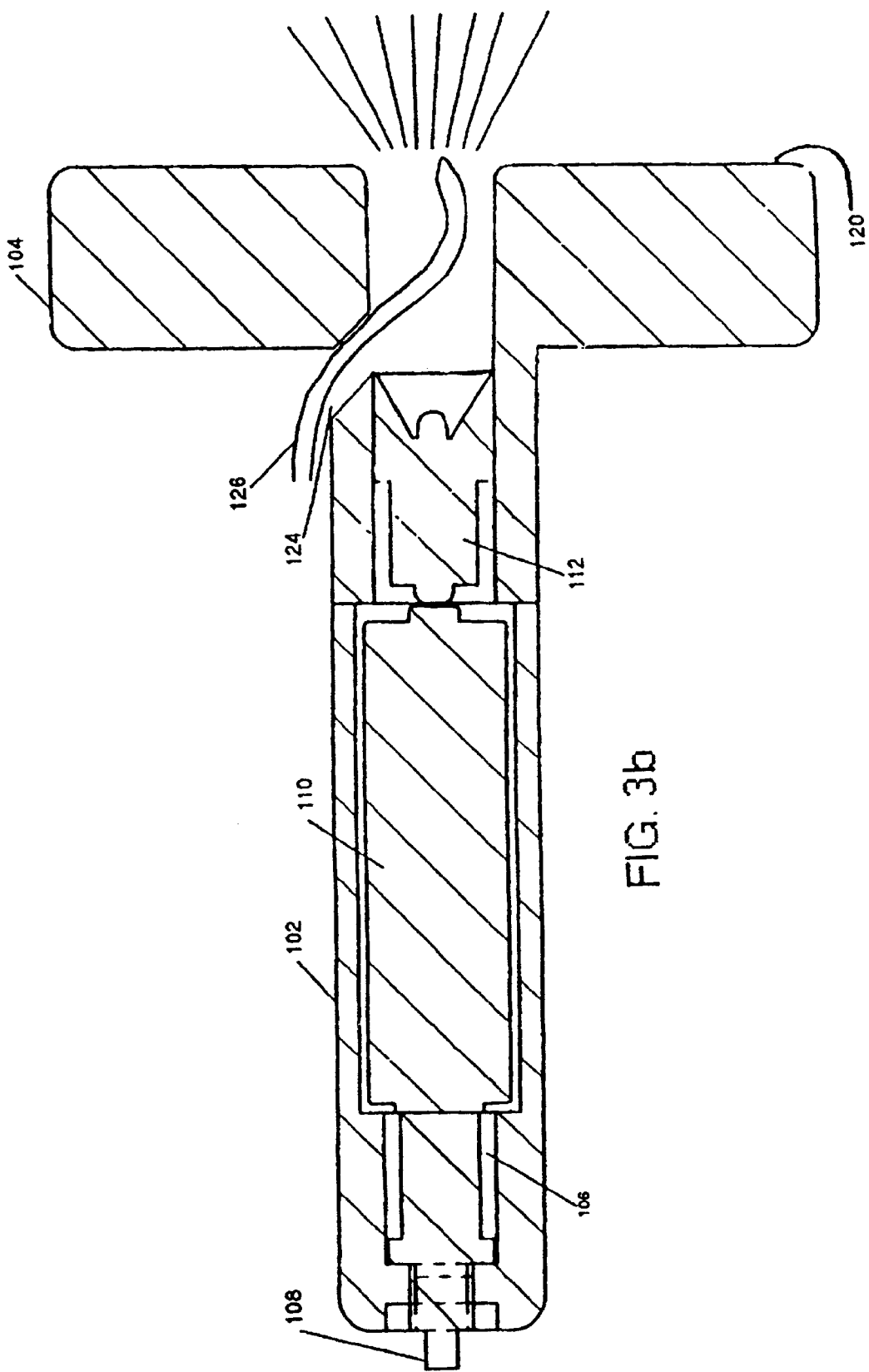
FIG. 3b is a cross-sectional side view of another embodiment of an applicator/placement device in accordance with the present invention the invention.

FIG. 3b shows another embodiment of an applicator/placement tool in accordance with the present invention. In a manner analogous to that described with respect to the access port 116 of the embodiment disclosed in FIGS. 1–3, the access port 124 also extends from the outer surface of the circular handle 102 to the compartment 106. This port 124 is sized to receive and hold a urinary catheter 126. The distal end of the catheter 126 is positioned flush against the outwardly facing surface 120 of the tool. The position of the catheter 126 in the tool still allows a quantity of light from the illumination source 112 to provide illumination at the outwardly facing surface 120 of the circular flange 104. The light emitted from the outwardly facing surface 120 of the circular flange 104 may be either focused or diffuse, depending on the type of illumination source 112, including possible lenses, used with the tool.

In operation, a user will insert the catheter 126 into the applicator/placement tool until the distal end of the catheter 126 is flush against the outwardly facing surface 120 of the tool. Once the catheter 126 is correctly positioned in the tool, the user may then actuate the push button switch 108, which closes the contacts between the battery 110 and the illumination source 112 and causes the illumination source 112 to generate light. Light from the illumination source 112 travels down through the compartment of the circular flange 104 and around the catheter 126, providing either diffuse or focused illumination at the outwardly facing surface 120 of the circular flange 104. The tool is then positioned at an angle relative to the meatus to allow the user to insert the catheter 126 through the meatus and into the bladder. After the distal end of the catheter 126 is secured to the bladder upon inflation of the balloon, the tool is removed and a urine collection bag is attached to the proximal end of the catheter 126.

In a preferred embodiment, the applicator or placement tool as disclosed in FIGS. 1–3b is made from a molded plastic material. However, other materials can be used, including metal, composite or any other material having the necessary structural characteristics to accomplish the function.

Figure 4A:
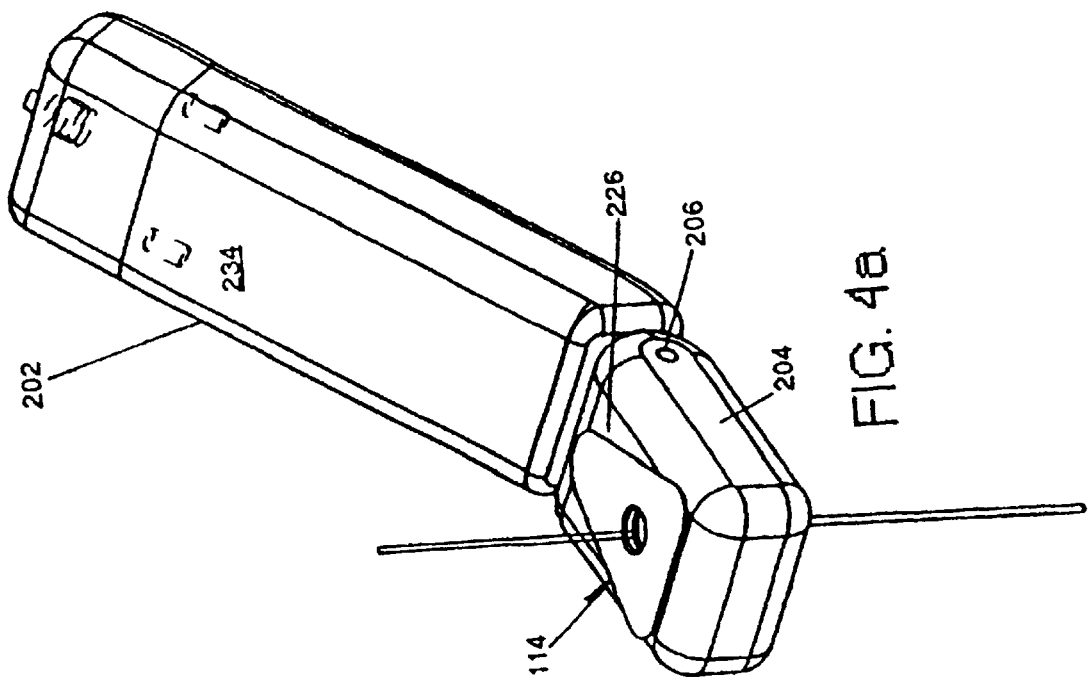
FIG. 4a is a perspective view of another embodiment of an applicator/placement device in accordance with the present invention.
Figure 4:
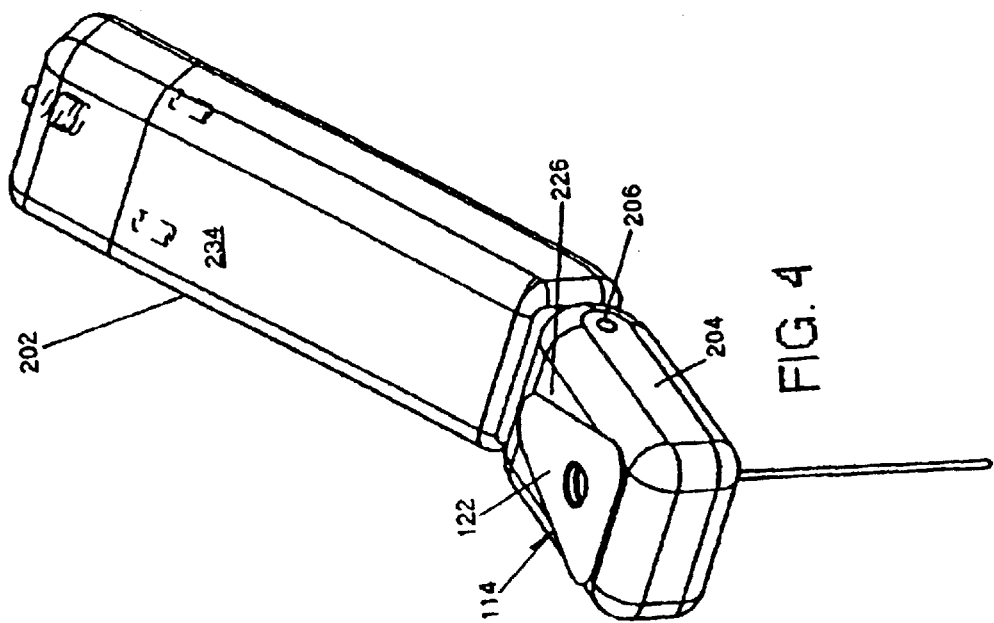
FIG. 4 is a perspective view of another embodiment of an applicator/placement device in accordance with the present invention.
Figure 5:
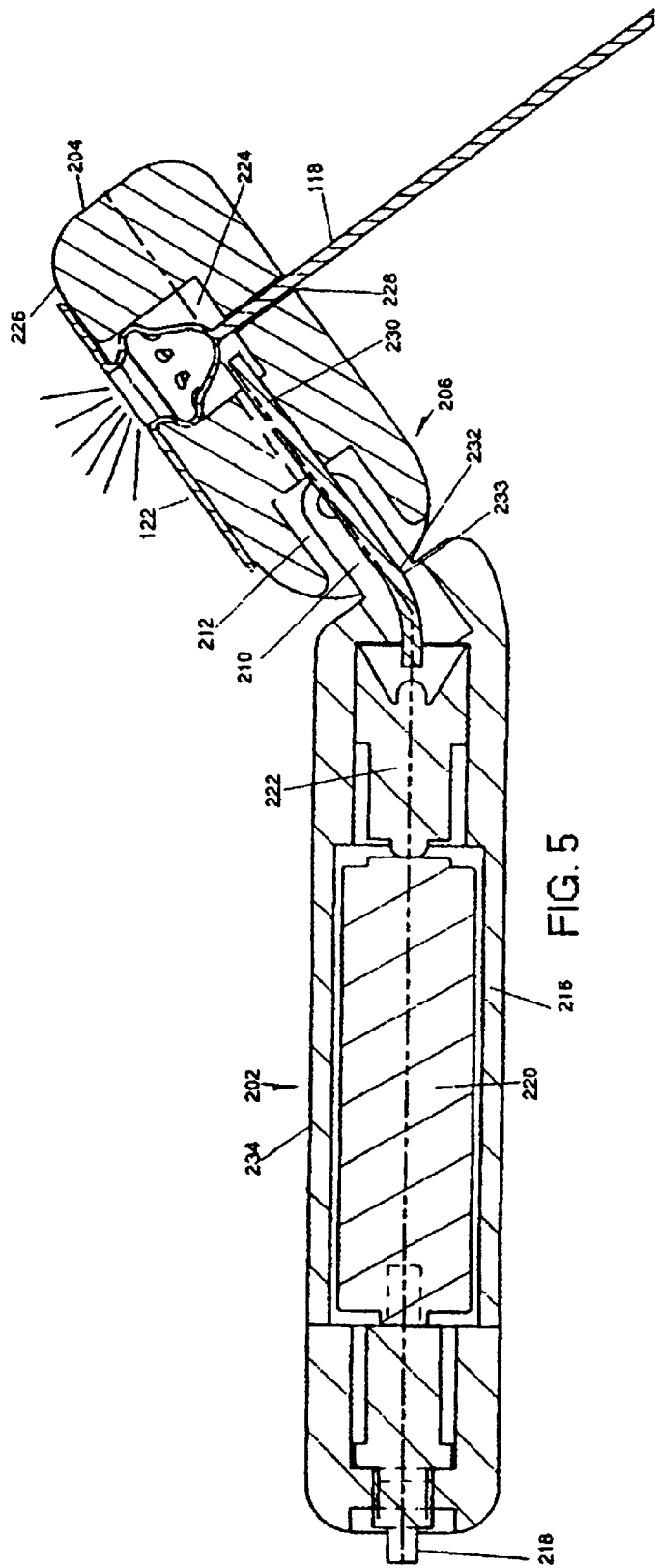
FIG. 5 is cross-sectional side view of another embodiment of an applicator/placement device in accordance with the present invention.
Figure 6:
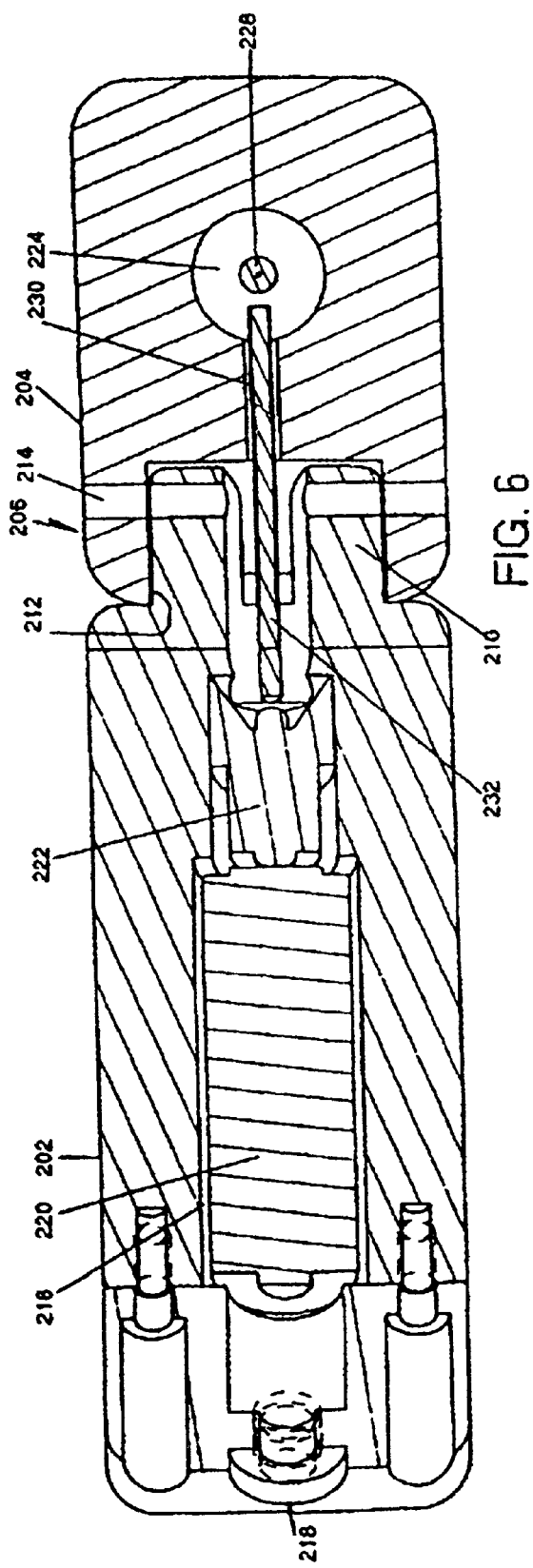
FIG. 6 is a cross-sectional view of another embodiment of an applicator/placement device in accordance with the present invention taken along the lines 6—6 of FIG. 5.

Referring now to FIGS. 4–6, another embodiment of an applicator/placement tool in accordance with the present invention includes an elongated, rectangular handle 202 and a rectangular, articulating flange 204 which are hinged to one another through a hinge assembly 206.

The hinge assembly 206 includes a tongue portion 210 which extends at an angle from one end of the handle 202 and is received in a groove region 212 of the articulating flange 204. The tongue portion 210 and the groove region 212 are then secured to one another with a pair of hinge pins 214 about which the handle 202 and articulating flange 204 pivot. In one embodiment, the fit between the tongue portion 210 and the groove region 212 is an interference fit so that movement of the articulating flange 204 relative to handle 202 is somewhat stiff and requires intentional effort by the user to achieve such movement. In another embodiment, the desired stiffness can be obtained by using pins 214 that are somewhat larger than the openings into which they are inserted in the flange 204 and handle 202.

In a manner analogous to that described with respect to the circular handle 102 of the embodiment disclosed in FIGS. 1–3, the handle 202 includes a compartment 216 which contains essentially three components, namely, a SPST push-button switch 218, a size AA battery power supply 220 and an illumination source 222. The compartment 216 extends substantially the entire length of the handle from the proximal end where the switch 218 is located to and through the distal end containing the tongue portion 210.

The articulating flange 204 is configured to have a recessed circular housing 224 extending into the flange 204 from a receiving surface 226 of the articulating flange 204 for receiving, for example, the incontinence device 114 which was discussed previously. In communication with the recessed circular housing 224 is an access port 228 that extends from the bottom of the recessed circular housing 224 to the opposite external surface of the articulating flange 204. This port is for the actuating line 118 of the incontinence device 114 and serves the same purpose as the access port 116 discussed in the previous embodiment.

Also in communication with the recessed circular housing 224 is an illumination access port 230 which extends from one side of the recessed circular housing 224 into the groove region 212 of the hinge assembly 206. The illumination access port 230 is in alignment with the distal end of the compartment 216 of the handle 202.

Positioned within the distal end of the compartment 216 of the handle 202 and the illumination access port 230 is a flexible optical fiber 232 which has one end placed in the compartment 216 a small distance from the illumination source 222 and the other end within the recessed circular housing 224 of the articulating flange 204. As so positioned, the optical fiber 232 is capable of transmitting light from the illumination source 222 to the recessed circular housing 224 regardless of the relative angular position of the handle 202 to the articulating flange 204.

The receiving surface 226 of the articulating flange 204 is configured to be a mirrored surface over substantially its entire surface area. Similarly, the top surface 234 of the handle 202 is also configured to have a mirrored surface, although not necessarily over substantially its entire surface area.

In operation the applicator/placement tool of this embodiment operates similarly to the embodiment disclosed in FIGS. 1–3. A user will mount the incontinence device 114 onto the applicator/placement tool by inserting the actuation line 118 through the access port 230. The user will then insert the top portion of the incontinence device 114 (in this case the valve portion 115) into the recessed circular housing 224 until the underside of the mounting flange 122 is in touching engagement with the receiving surface 226 of the articulating flange 204. The user may then apply tension to the actuation line 118 to ensure that the incontinence device 114 is securely mounted onto the tool.

Once the incontinence device 114 is mounted the user may then actuate the push-button switch 218, which closes the contacts between the battery 220 and the illumination source 222 and causes the illumination source 222 to generate light. Light from the illumination source 222 then travels down through the distal end of the compartment 206 of the handle 202 and into the optical fiber 232. The optical fiber 232 then transmits the light into the recessed circular housing 224. Since the incontinence device 114 is translucent, a quantity of light from the light source 222 will be diffused through the incontinence device 114 so as to provide illumination at the receiving surface 226 of the articulating flange 204, as shown in FIG. 5. Alternatively, as shown in FIGS. 4a and 5a, the illumination source 222, possibly in combination with a lens or lenses (not shown), may be configured to generate a focused beam of light through the incontinence device 114. As shown in FIG. 5a, the optical fiber 232 is bent at a 90° angle 233 and its distal end is aligned with a hole in the external incontinence device 114. The focused beam of light passes therethrough and provides improved illumination at the specific targeted area.

If not previously performed, the user will then remove any protective material from the exposed side of the external incontinence device 114 and expose the adhesive that is coated on the exposed side. The user will then orient the device 114 in a manner such that the light emanating from the recessed circular housing 224 of the articulating flange 204 is directed toward the urinary meatus.

In this embodiment, the tool offers versatility to the user during the step of orienting the device 114 towards the urinary meatus insofar as the user may pivot the articulating flange 204 into whatever angular relationship offers the best visualization of the meatus. The visualization is further enhanced by the presence of two mirrored surfaces, one on the articulating flange 204 and one on the top surface 234 of the handle 202. In this manner, the user can then position the external continence device 114 such that the opening for directing the urine can be placed precisely over the meatus. The user will then move the tool so that the adhesive contacts the body. Upon withdrawing the tool, the incontinence device 114 is then removed from the tool and remains secured to the user in a manner that ensures proper treatment of the incontinence.

Figure 5B:
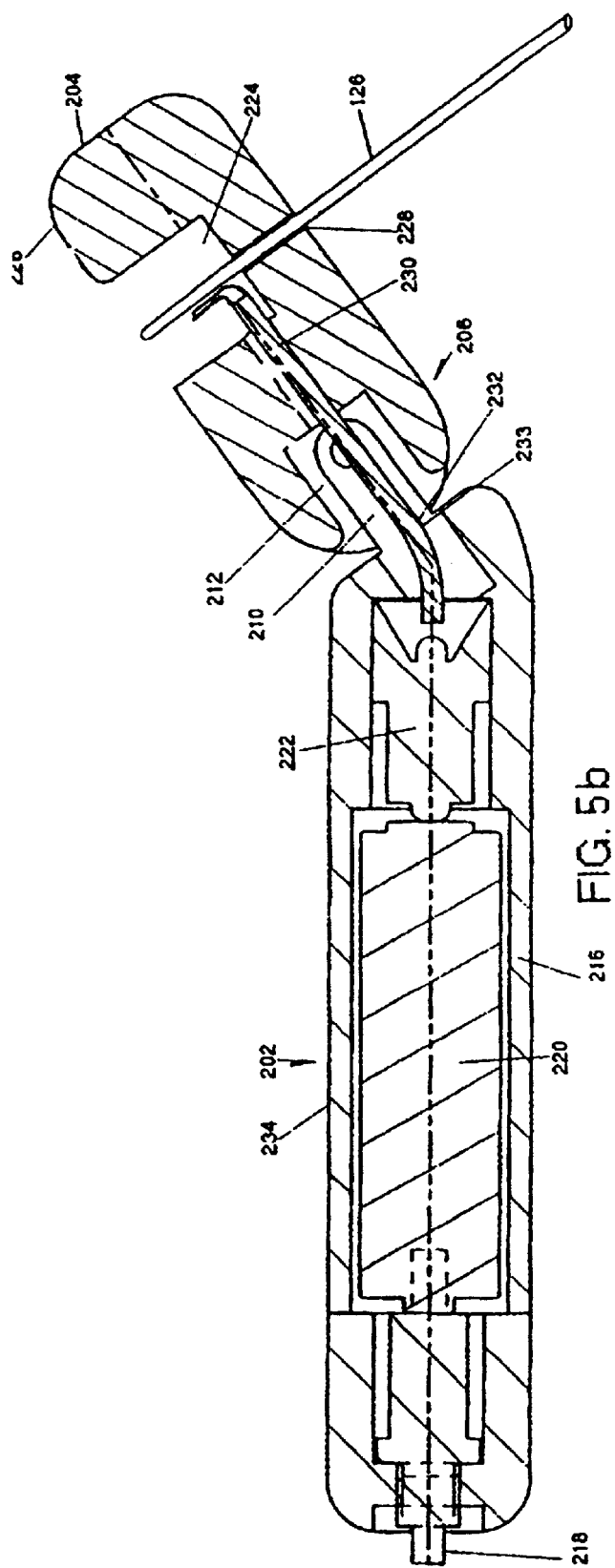
FIG. 5b is a cross-sectional side view of another embodiment of an applicator/placement device in accordance with the present invention.

FIG. 5b shows another embodiment of an applicator/placement tool in accordance with the present invention. In a manner analogous to that described with respect to the access port 228 of the embodiment disclosed in FIGS. 4–6, the access port 236 also extends from the bottom of the recessed circular housing 224 to the opposite external surface of the articulating flange 204. This port 236 is sized to receive and hold a urinary catheter 126. The distal end of the catheter 126 is positioned flush against the receiving surface 226 of the articulating flange 204. The position of the catheter 126 in the tool still allows the optical fiber 232 to transmit light from the illumination source 222 to the recessed circular housing 224. The light emitted from the recessed circular housing 224 of the articulating flange 204 may be either focused or diffuse, depending on the type of illumination source 222, including possible lenses, used with the tool.

In operation, a user will insert the catheter 126 into the applicator/placement tool until the distal end of the catheter 126 is flush against the recessed circular housing 224 of the tool. Once the catheter 126 is correctly positioned in the tool, the user may then actuate the push button switch 218, which closes the contacts between the battery 220 and the illumination source 222 and causes the illumination source 222 to generate light. Light from the illumination source 222 travels down through the distal end of the compartment 206 of the handle 202 and into the optical fiber 232. The optical fiber 232 then transmits the light into the recessed circular housing 224 and around the catheter 126, providing either diffuse or focused illumination at the receiving surface 226 of the articulating flange 204. The tool is then positioned at an angle relative to the meatus to allow the user to insert the catheter 126 through the meatus and into the bladder. After the distal end of the catheter 126 is secured to the bladder upon inflation of the balloon, the tool is removed and a urine collection bag is attached to the proximal end of the catheter 126.

In a preferred embodiment, the applicator or placement tool as disclosed in FIGS. 4–6 is made from a molded plastic material. However, other materials can be used, including metal, composite or any other material having the necessary structural characteristics to accomplish the function.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An external tool for external placement of a bladder output
   control device capable of controlling bladder output without any structure projecting into
   a user's urethra, the tool comprising:
   a handle portion for gripping said tool;
   a flange extending perpendiculary from said handle portion;
   said flange having a planar top surface for mating with a planar mounting surface of said bladder output control device;
   a compartment disposed in at least said handle portion for housing an illumination device;
   said illumination device positioned in said compartment so as to provide illumination at said planar top surface for holding said bladder output control device; and
   a pathway disposed in said flange, said pathway sized to receive an actuation line extending from said bladder output control device.

2. A tool according to claim 1, wherein said bladder output control device is an external incontinence device.

3. A tool according to claim 1, wherein said planar top surface is mirrored.

4. A tool according to claim 3, wherein said planar top surface is mirrored over substantially entirely all of an area of said planar top surface.

5. An external tool for external placement of a bladder output control device comprising:
   a handle portion for gripping said tool;
   a flange extending from said handle portion;
   said flange having a planar top surface for mating with a planar mounting surface of said bladder output control device;
   a compartment disposed in at least said handle portion for housing an illumination device;
   said illumination device positioned in said compartment so as to provide illumination at said planar top surface for holding said bladder output control device; and
   a pathway disposed in said flange, said pathway sized to receive an actuation line extending from said bladder output control device,
   wherein said flange is pivotally connected to said handle portion such that said flange may be selectively positioned at an angle relative to said handle.

6. A tool according to claim 5, wherein said flange includes a recessed housing for receiving at least a portion of said bladder output control device and wherein said flange includes an illumination port between said recessed housing and said compartment.

7. A tool according to claim 6, wherein said illumination device includes a optical fiber extending from said compartment through said illumination port to said recessed housing.

8. A tool according to claim 1, wherein said illumination is focused.

9. A tool according to claim 1, wherein said handle is circular.

10. A tool according to claim 9, wherein said flange is circular and wherein said flange has a greater diameter than said handle.

11. A tool according to claim 10, wherein said compartment extends through said flange.

12. An external device for external placement of an external bladder output control device capable of controlling bladder output without any structure projecting into a user's urethra, the external device comprising:
    a handle; a flange extending perpendicularly from said handle; said flange having a planar top surface;
    said planar top surface mates with a planar mounting surface of said external bladder output control device;
    a pathway disposed in said handle,
    said pathway sized to receive an actuation line extending from said bladder output control device; and
    an illumination device mounted on said handle providing illumination at least at said planar top surface.

13. A tool according to claim 12, wherein said bladder output control device is an external incontinence device.

14. A tool according to claim 12, wherein said planar top surface is mirrored.

15. A tool according to claim 12, wherein said planar top surface is mirrored over substantially entirely all of an area of said planar top surface.

16. A tool according to claim 12, wherein said handle includes a compartment for housing said illumination device.

17. A tool according to claim 16, wherein said tool includes a flange connected to said handle and wherein said planar top surface is disposed on said flange.

18. An external device for external placement of an external bladder output control device comprising:
    a handle;
    a planar top surface fixed to said handle which mates with a planar mounting surface of said bladder output control device;
    a pathway disposed in said handle, said pathway sized to receive an actuation line extending from said bladder output control device;

an illumination device mounted on said handle providing illumination at least at said planar top surface, a flange connected to said handle, wherein said flange is pivotally connected to said handle such that said flange may be selectively positioned at an angle relative to said handle.

19. A tool according to claim 18, wherein said flange includes a recessed housing for receiving at least a portion of said bladder output control device and wherein said flange includes an illumination port between said recessed housing and said compartment.

20. A tool according to claim 19, wherein said illumination device includes an optical fiber extending from said compartment through said illumination port to said recessed housing.

21. A tool according to claim 12, wherein said handle is circular.

22. A tool according to claim 21, wherein said flange is circular and wherein said flange has a greater diameter than said handle.

23. A tool according to claim 22, wherein said compartment extends through said flange.

24. A tool according to claim 12, wherein said illumination is focused.

25. A method of externally placing an external bladder output control device on the body of a user comprising the steps of:

holding a handle of a placement tool wherein said handle has a planar top surface for mating with a planar mounting surface of said bladder output control device;

affixing said planar mounting surface of bladder output control device on said planar top surface including directing an actuator line of said bladder output control device through said handle;

directing said bladder output control device toward a urinary meatus of a user;

activating an illumination device mounted on said placement tool either prior to or after said directing step, said activation providing illumination at said planar top surface;

visualizing a location of said bladder output control device relative to said urinary meatus;

placing said bladder output control device over said urinary meatus;

moving said bladder output control device into contact with the body; and, withdrawing said placement tool from said body.

26. A method according to claim 25, wherein said bladder output control device is an external incontinence device.

27. A method according to claim 25, wherein said placement tool includes a flange connected to said handle and wherein said planar top surface is disposed on said flange.

28. A method according to claim 27, wherein prior to said placing step, said flange is pivoted relative to said handle to better aid in performing said step of visualizing.

29. A method according to claim 25, wherein said planar top surface is mirrored and said visualizing step includes viewing said meatus on said mirrored surface.

30. A method according to claim 25, wherein said illumination device is mounted on said handle and wherein said activating step causes the generation of light from an internal compartment on said handle.

* * * * *